(12) United States Patent
Nagel et al.

(10) Patent No.: US 12,704,457 B2
(45) Date of Patent: Aug. 11, 2026

(54) HYPERSPECTRAL SOIL SAMPLING APPARATUS TO PRODUCE SOIL MAPS

(71) Applicants: Penelope Kathleen Nagel, San Diego, CA (US); Cheryl Deann Rice, San Diego, CA (US); Kenneth George Stalker, La Jolla, CA (US); Brian Zamudio, La Jolla, CA (US)

(72) Inventors: Penelope Kathleen Nagel, San Diego, CA (US); Cheryl Deann Rice, San Diego, CA (US); Kenneth George Stalker, La Jolla, CA (US); Brian Zamudio, La Jolla, CA (US)

( * ) Notice: Subject to any disclaimer, the term of this patent is extended or adjusted under 35 U.S.C. 154(b) by 230 days.

(21) Appl. No.: 18/667,732

(22) Filed: May 17, 2024

(65) Prior Publication Data

US 2024/0393237 A1 Nov. 28, 2024

Related U.S. Application Data

(60) Provisional application No. 63/503,461, filed on May 20, 2023.

(51) Int. Cl.

| | |
|---|---|
| ***G01N 23/00*** | (2006.01) |
| ***G01N 1/08*** | (2006.01) |
| ***G01N 1/28*** | (2006.01) |
| ***G01N 1/38*** | (2006.01) |
| ***G01N 21/3563*** | (2014.01) |
| ***G01N 33/24*** | (2006.01) |
| *G01N 21/35* | (2014.01) |

(52) U.S. Cl.

CPC ........... *G01N 21/3563* (2013.01); *G01N 1/08* (2013.01); *G01N 1/286* (2013.01); *G01N 1/38* (2013.01); *G01N 33/245* (2024.05); *G01N 2021/3595* (2013.01); *G01N 2201/08* (2013.01); *G01N 2201/127* (2013.01)

(58) Field of Classification Search

CPC ............ G01N 1/08; G01N 1/286; G01N 1/38; G01N 2021/3595; G01N 21/3563; G01N 2201/08; G01N 2201/127; G01N 33/245; G01N 33/24

See application file for complete search history.

(56) References Cited

U.S. PATENT DOCUMENTS

2017/0370064 A1* 12/2017 Morgan .................. G01J 3/108
2023/0119569 A1* 4/2023 Koch .................. A01C 21/007 702/2

* cited by examiner

*Primary Examiner* — Dani Fox

(57) ABSTRACT

Disclosed is a soil sampling device designed to enhance efficiency and accuracy in soil analysis processes. The soil sampling device includes a computer system for data storage and processing, along with a display screen for visualizing collected scan data. Equipped with a GPS sensor, the device precisely identifies soil sampling locations. A sampling chamber ensures sample integrity by blocking ambient light during spectroscopy readings and facilitates sample disposal post-testing. Operating with a core rod column and an auger, the device efficiently extracts soil samples while homogenizing materials. A driver mechanism propels the auger, supported by a homogenization cylinder for mixing soil samples. Additional features include a stomp pad for depth control during sampling, a calibration standard mechanism for sensor calibration, and an sampling element/auger cover for sample containment. The soil sampling device ensures ease of use, maintenance, and accurate soil analysis, contributing to improved agricultural practices and environmental monitoring.

20 Claims, 10 Drawing Sheets

HYPERSPECTRAL SOIL SAMPLING APPARATUS TO PRODUCE SOIL MAPS

BACKGROUND

Technical Field

The invention presented herein is generally directed toward a soil sampling device. More particularly, but not limited to, a soil sampling device and method for creating more rapid and accurate soil maps to more efficiently enable the user to determine soil content.

Description of the Related Art

In the agricultural sector, inefficient fertilizer use leads to approximately 5.7 billion dollars in lost crop yields and 1.7 billion dollars in excess costs. Current practices rely on nutrient maps generated from data derived from grid soil sampling, yield maps, and/or satellite imagery of crops in growth. However, conventional grid soil sampling and laboratory analyses lack the granularity required, are time-consuming and incur high costs. The labor-intensive and imprecise nature of nutrient maps created through grid soil sampling further compounds these challenges. Despite efforts to adopt computer-generated nutrient maps for variable rate fertilizer application, their production remains costly and inefficient, limiting their widespread adoption in farming. In the United States alone, approximately 1.5 billion dollars are spent annually on grid sampling, with an average loss of 50 hours per year on a 10,000-acre farm due to labor-intensive sampling methods. However, the potential benefits of optimized nutrient mapping—such as an estimated 15% reduction in fertilizer costs and a 13% increase in crop yields—present a compelling incentive for modern farmers to explore more efficient techniques.

Unfortunately, current soil mapping methods suffer from inefficiency, high costs, and time consumption, leading many farms to forgo their use altogether and apply incorrect amounts of fertilizer, resulting in suboptimal field performance and waste of resources.

This disclosure recognizes the necessity for a soil sampling device and method that adheres to standardized processes and procedures for soil analysis, particularly in the creation of rapid and precise soil maps. By facilitating the user's ability to efficiently determine soil content, these solutions aim to address the aforementioned challenges effectively.

Thus, in view of the above, there is a long-felt need in the industry to address the aforementioned deficiencies and inadequacies.

The approaches described in this section are approaches that could be pursued, but these are not necessarily approaches that have been previously conceived or pursued. Therefore, unless otherwise indicated, it should not be assumed that any of the approaches described in this section qualify as prior art merely by virtue of their inclusion in this section.

SUMMARY

A soil sampling device and method to produce soil nutrient maps are provided, as shown in and/or described in connection with at least one of the figures.

One aspect of the present disclosure relates to a soil sampling device that includes a computer system; equipment housing; a GPS sensor; a sampling chamber; a core rod column and an auger; a driver mechanism; a homogenization cylinder; a stomp pad; a calibration standard mechanism; a sampling element/auger cover; a quick disconnect; spectral sensors and FTIR engine; and a probe consisting of a light source and fiber optic cable. The computer system is configured to store and process data related to the location of soil sampling and spectral data and to display the collected scan data on a display screen. The equipment housing is configured to support the computer system. The GPS sensor is housed in the equipment housing to identify a location to extract the soil sample. The sampling chamber is configured to store the soil sample during one or more scans, which blocks ambient light to ensure accurate spectroscopy readings and provides a mechanism to support the disposal of the soil sample after testing. The core rod column and the auger are configured to extract the soil sample. The auger is configured to cut the soil, migrate the soil upward to the sampling chamber, and homogenize the material in the first stage. The driver mechanism is housed in the equipment housing to drive the auger and core rod column to extract the soil sample. In another aspect, the auger may be reversed to eliminate residual material in preparation for subsequent sampling. The homogenization cylinder is configured to support the equipment housing and the sampling chamber. The homogenization cylinder encloses the auger and the driver mechanism and provides an area for mixing and homogenization of the soil sample. The stomp pad is configured to control the depth of the soil sampling and to provide support during the actuation of the auger. The calibration standard mechanism is configured to move a calibration standard in and out of view of a probe consisting of a light source and fiber optic cable for calibration. The calibration standard mechanism includes a cleaning strip to wipe the residue or the probe consisting of a light source and fiber optic cable before calibration to ensure accuracy. The sampling element/auger cover is configured to retract and advance during the soil sample collection to ensure sample capture and containment. The quick disconnect is configured to allow for the removal of the auger for cleaning and removing debris. The probe consisting of a light source and fiber optic cable is configured to scan the soil sample. The spectral sensors and FTIR engine are configured to collect spectral data using the probe output.

In an aspect, the computer system comprises a processor configured to calibrate a plurality of sensors using a plurality of software algorithms.

In an aspect, the equipment housing houses a plurality of components comprising: one or more hyperspectral sensors (IR, NIR, SWIR), a plurality of batteries, an FTIR engine, a GPS scanner and an auger motor to drive the auger.

In an aspect, the sampling chamber comprises a light and a fiber optic cable.

In an aspect, the sampling element is a motor-driven auger-type device, capable of pulling a specified volume sample over a fixed depth (1-30 inches).

In an aspect, the sampling element is a manual tube, capable of pulling the specified volume sample over the fixed depth (1-30 inches).

In an aspect, the auger or the sampling element/auger cover retracts and advances to a specified depth during use to allow for sample capture and containment.

In an aspect, the soil sampling device includes either a spring-loaded or an actuated cover for the auger.

In an aspect, the spring-loaded or actuator comprises a stop to control a sampling depth.

In an aspect, the stomp pad is configured to control the depth of the auger and to facilitate the operational stability of the soil sampling device.

In an aspect, the auger is attached to a motor drive via the quick disconnect.

In an aspect, the homogenization cylinder comprises an opening to allow for cleaning and removal of debris.

In an aspect, the sampling element/auger homogenizes the soil sample during transport through the homogenization cylinder to the sampling chamber.

In an aspect, the sampling element/auger and the homogenization cylinder capture the soil sample in its entirety and transport it to the sampling chamber.

Another aspect of the present disclosure relates to a method to create one or more soil maps by collecting one or more soil samples. The method includes a step of initiating, by a processor, an operation of a computer system. The method includes a step of capturing, by a probe consisting of a light source and fiber optic cable, a scan of a surface by moving a calibration standard in front of the probe. The method includes a step of calibrating, by the processor, a plurality of spectral sensors by using the captured scan. The method includes a step of recording, by the processor, a sample location using a GPS sensor. The method includes a step of activating, by the processor or the motor drive controls, an auger motor and placing the auger at the sample location. The method includes a step of extending downward a core rod column and/or auger into the soil to an appropriate depth and drawing up a sample core. The method includes a step of pulling the soil by the auger into a homogenization cylinder, wherein as the material rotates, it passes the first stage of homogenization. The method includes a step of moving the soil sample upward through the homogenization cylinder and depositing the soil sample into a sampling chamber. The method includes a step of initiating a scan by the spectral sensors whose data is supplied to the computer system. In an aspect, the probe consisting of a light source and fiber optic cable and sensors scan the soil sample. The method includes a step of opening a slide on the bottom of the sampling chamber by the user, allowing the soil sample to be deposited back in the field or a bag if required. The method optionally includes a step of homogenizing the soil sample exiting the auger and entering the sample chamber, thereby resulting in a second stage homogenization of the soil sample.

In an aspect, the sampling element is a motor-driven auger-type device, capable of extracting a specified volume sample at a fixed depth ranging from 1 to 30 inches.

In an aspect, the sampling element or the auger is a manual tube, capable of extracting the specified volume sample at a fixed depth ranging from 1 to 30 inches.

In an aspect, the auger or sampling element/auger cover is configured to retract and advance to a specified depth during operation to facilitate sample collection and containment. In another aspect, the auger may be reversed to eliminate residual material in preparation for subsequent sampling.

In an aspect, the stomp pad is configured to regulate the depth of the auger and enhance the operational stability of the soil sampling device.

Accordingly, one advantage of the present invention is that it is used for the hyperspectral analysis of soil samples, enabling the determination of elemental contents such as Soil Organic Carbon (SOC), Nitrogen, Phosphorus, Potassium, Calcium, Magnesium, Manganese, Boron, Zinc, Sulfur, Soil Organic Matter (SOM), Iron, Copper, Sodium, pH, and cation exchange capacity (CeC). The device is purposefully designed to facilitate rapid sampling with immediate feedback on soil content, aiding in the assessment of nutrient requirements. While numerous soil testing methods/devices are currently employed, this device distinguishes itself by providing real-time feedback during sampling, unlike traditional methods that entail sample collection and transportation to an external testing laboratory for analysis.

Accordingly, one advantage of the present invention is that it simplifies sampling and allows for multiple test readings to be taken within a given sampling location to provide an accurate mapping of the soil nutrient content of the area tested. The objective is to provide an all-in-one device that samples, analyzes and reports the data in real-time in the field, which can be transported and operated as a standalone unit by a single individual without the aid of larger farm implements or equipment.

Accordingly, another advantage of the present invention is that it specifically meets the testing requirements defined in ASTM D8438/D8438M-23 Standard test methods for the use of hyperspectral sensors for soil nutrient analysis of ground-based samples.

Other embodiments and advantages will become readily apparent to those skilled in the art upon viewing the drawings and reading the detailed description hereafter, all without departing from the scope of the disclosure. The drawings and detailed descriptions presented are to be regarded as illustrative in nature and not in any way as restrictive.

Other features of the example embodiments will be apparent from the drawings and from the detailed description that follows.

BRIEF DESCRIPTION OF THE DRAWINGS

The accompanying drawings illustrate the embodiments of systems, methods, and other aspects of the disclosure. Any person with ordinary skills in the art will appreciate that the illustrated element boundaries (e.g., boxes, groups of boxes, or other shapes) in the figures represent an example of the boundaries. In some examples, one element may be designed as multiple elements, or multiple elements may be designed as one element. In some examples, an element shown as an internal component of one element may be implemented as an external component in another and vice versa. Furthermore, the elements may not be drawn to scale.

Various embodiments will hereinafter be described in accordance with the appended drawings, which are provided to illustrate, not limit, the scope, wherein similar designations denote similar elements, and in which.

DETAILED DESCRIPTION

Figure 1:
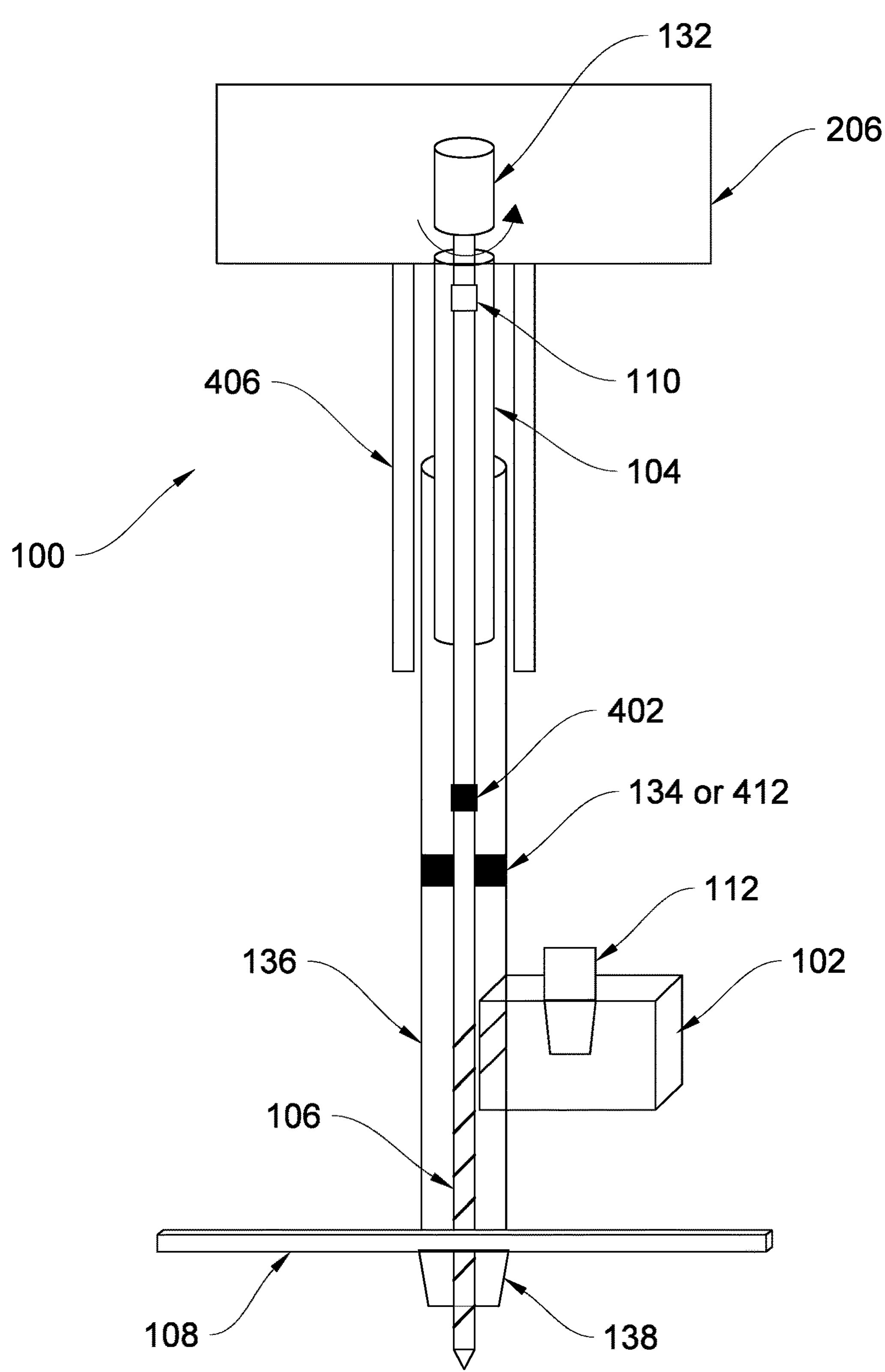
FIG. 1 illustrates an exploded view of a soil sampling device, in accordance with one embodiment of the present invention.

The present description is best understood with reference to the detailed figures and description set forth herein. Various embodiments of the present system and method have been discussed with reference to the figures. However, those skilled in the art will readily appreciate that the detailed description provided herein with respect to the figures are merely for explanatory purposes, as the present system and method may extend beyond the described embodiments. For instance, the teachings presented and the needs of a particular application may yield multiple alternative and suitable approaches to implement the functionality of any detail of the present systems and methods described herein. Therefore, any approach to implement the present system and method may extend beyond certain implementation choices in the following embodiments.

According to an embodiment herein, the methods of the present invention may be implemented by performing or completing manually, automatically, and/or a combination of thereof. The term "method" refers to manners, means, techniques, and procedures for accomplishing any task including, but not limited to, those manners, means, techniques, and procedures either known to the person skilled in the art or readily developed from existing manners, means, techniques and procedures by practitioners of the art to which the present invention belongs. The persons skilled in the art will envision many other possible variations within the scope of the present system and method described herein.

At a high level, aspects of the present disclosure are directed to a method for collecting soil samples utilizing hyperspectral sensors begins with activating the computer and bringing the software online. The calibration standard is positioned in front of the probe consisting of a light source and fiber optic cable, and a scan is conducted to calibrate the sensor. The computer system synchronizes with the GPS to record the sample location. Subsequently, the auger motor is engaged, and the auger is positioned at the designated sample site. The motorized auger/homogenization cylinder descends into the soil to the desired depth, retrieving the sample core. As the auger pulls the soil into the homogenization cylinder, rotational motion initiates the first stage of homogenization. The sample is then elevated through the homogenization cylinder and deposited into the sampling chamber. Material exiting the auger undergoes the second stage of homogenization. The sample volume is adjusted to ensure contact with the probe consisting of a light source and fiber optic cable face. The computer system initiates the scan, and the probe consisting of a light source and fiber optic cable scans the sample and provides the light to the spectral sensors and FTIR engine. Upon completion, the user can release the sample into the field or a bag via a slide on the sample chamber. The auger can then be reversed to eliminate residual material in preparation for subsequent sampling. The device then proceeds to the next sample location to repeat the process for a new sample.

FIG. 1 illustrates an exploded view of a soil sampling device (100), in accordance with one embodiment of the present invention. FIGS. 1-4 are explained in conjunction with FIGS. 5-9. The soil sampling device (100) includes a computer system (202); an equipment housing (206); a GPS sensor (902); a sampling chamber (102); a core rod column (104) an auger (106); a driver mechanism (904); a stomp pad (108); a calibration standard mechanism (906); a sampling element/auger cover (908); a quick disconnect (110); probe consisting of a light source and fiber optic cable (112); a drill motor (132; a homogenization cylinder/column (136); and a sampling tip (138).

The computer system (202) is configured to store and process data related to the location of soil sampling and spectral data and to display the collected scan data on a display screen (204). In an embodiment, the computer system (202) comprises a processor (910) configured to calibrate a plurality of spectral sensors (912) using a plurality of software algorithms. Examples of the computer system (202) include but are not limited to a smartphone, a mobile device, a computing device, or a computer.

Figure 2:
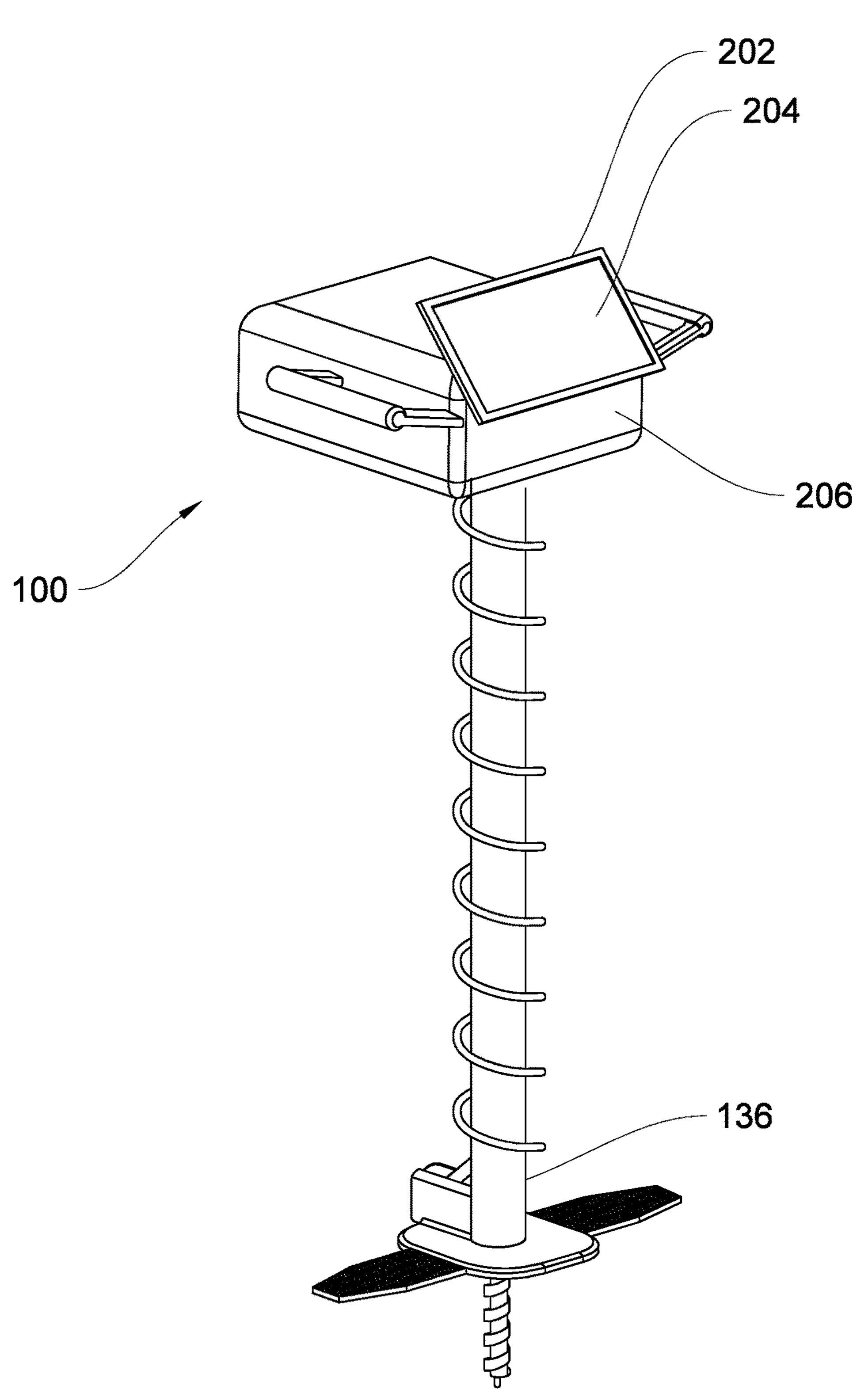
FIG. 2 illustrates an assembled view of the soil sampling device, in accordance with one embodiment of the present invention.
Figure 3:
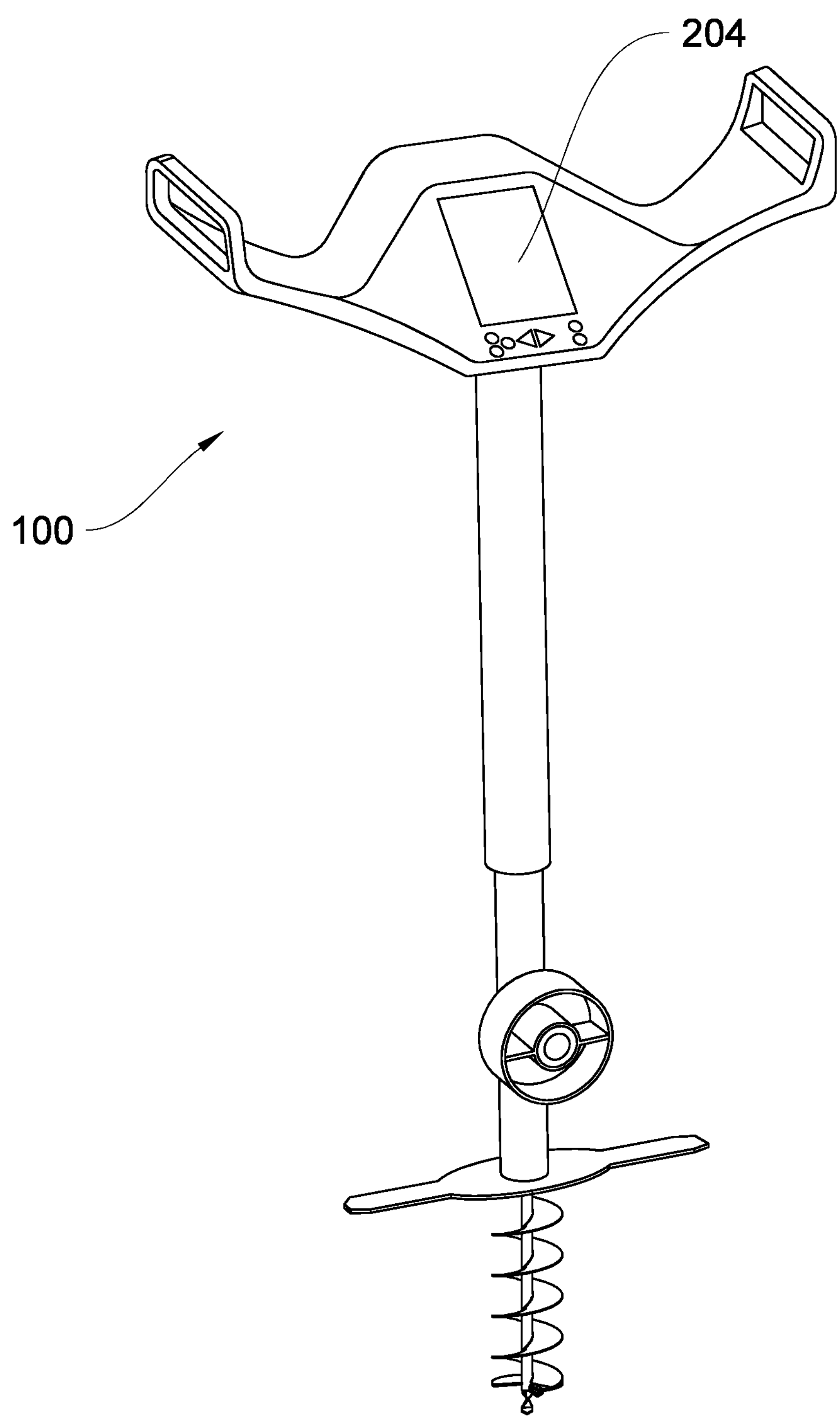
FIG. 3 illustrates an alternative view of the soil sampling device, in accordance with one embodiment of the present invention.
Figure 4:
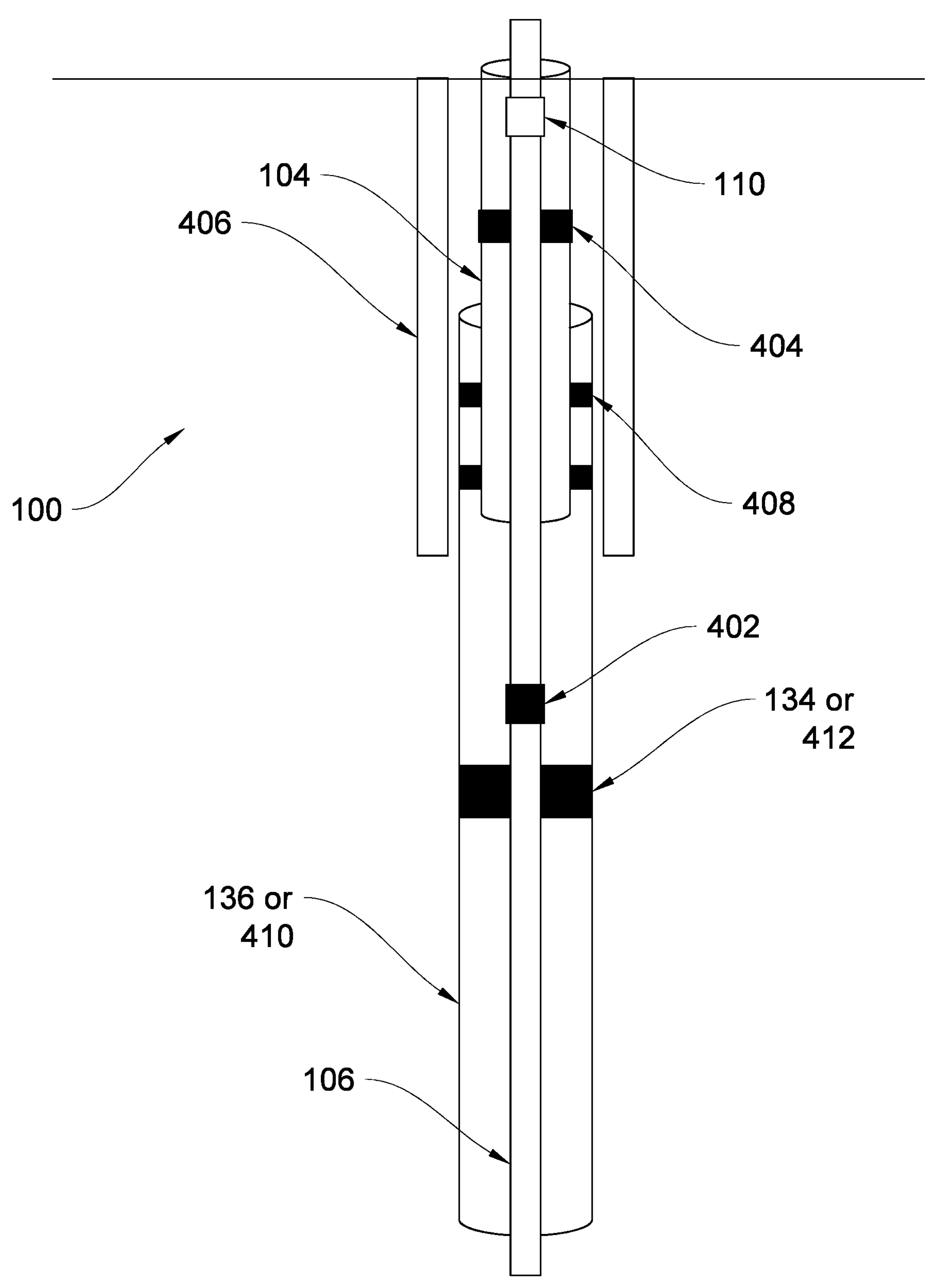
FIG. 4 illustrates a partial view of the soil sampling device, in accordance with one embodiment of the present invention.

FIG. 2 illustrates an assembled view of the soil sampling device (100), in accordance with one embodiment of the present invention. In an embodiment, the soil sampling device (100) can be manually operated is portable, and can be hand-carried between locations. In an embodiment, the soil sampling device (100) weighs approximately 35 lbs. and can easily be moved and maneuvered by a single operator. Further, the soil sampling device (100) is manually placed on the level surface to be sampled and is held vertically (perpendicular to the surface) by the operator during sampling. The individual location is measured via GPS sensor and the location for each sample is stored as part of the software program or algorithms. FIG. 3 illustrates an alternative view of the soil sampling device (100), in accordance with one embodiment of the present invention. In an embodiment, the soil sampling device (100) is operated in an automated mode in which the sampling device (100) is encased in a portable package that can be transported to each sampling site. This could be via truck, tractor, off-road vehicle, or the like. The soil sampling device is driven to the sampling site and is placed on the level surface to be sampled. The sampling element (auger) is held vertically (perpendicular to the surface) by the soil sampling device during sampling. The individual location is measured via a GPS sensor and the location for each sample is stored as part of the software program. FIG. 4 illustrates a partial view of the soil sampling device (100), in accordance with one embodiment of the present invention. FIG. 4 depicts coring rod column bushing (404); a spring or hydraulic actuator (406); a plurality of column interface bushings (408); a homogenization cylinder (136); and a plurality of sampling column bushings (412).

Figure 6:
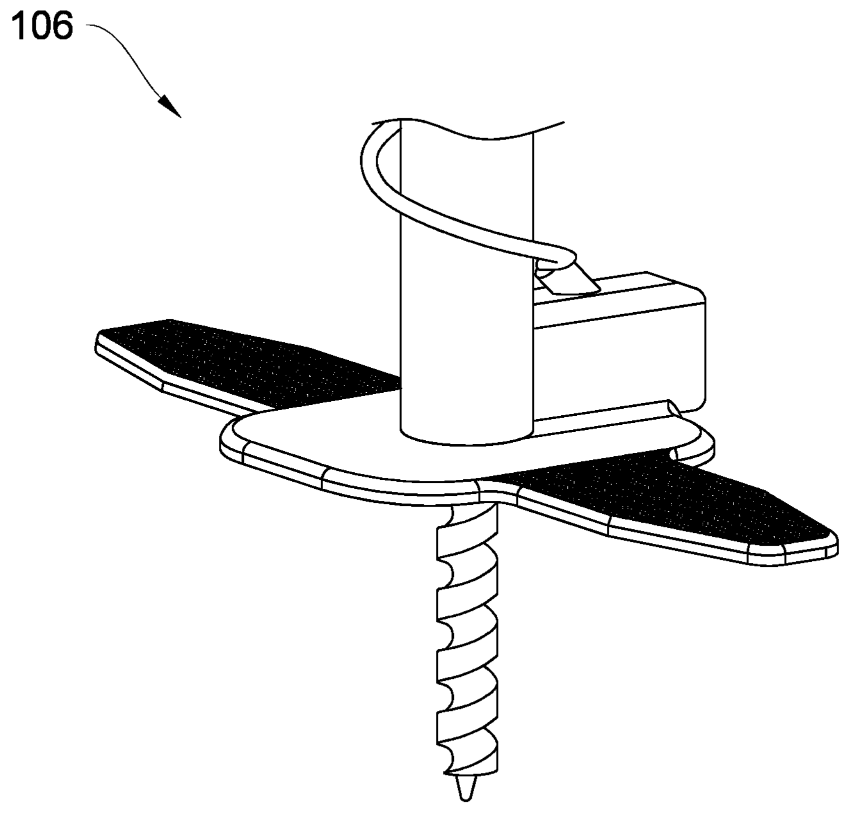
FIG. 6 illustrates a closer view of the auger, in accordance with one embodiment of the present invention.
Figure 7:
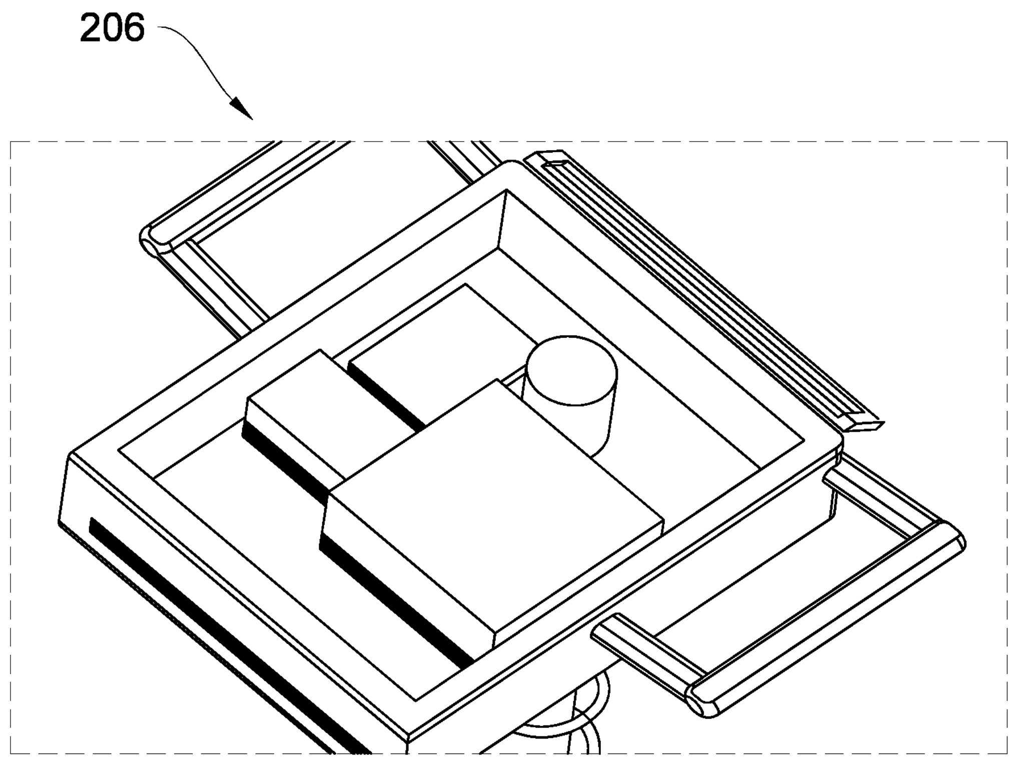
FIG. 7 illustrates a perspective view of an equipment housing with hand holds, in accordance with at least one embodiment.

FIG. 7 illustrates a perspective view of an equipment housing (206) with hand holds, in accordance with at least one embodiment. The equipment housing (206) is configured to support the computer system (202). FIG. 9 illustrates various components of the present soil sampling device that are not depicted in FIGS. 1-8, in accordance with at least one embodiment. In an embodiment, the equipment housing (206) houses a plurality of components comprising: one or more hyperspectral sensors (IR, NIR, SWIR) (914), a plurality of batteries (918), an FTIR engine (920), and an auger motor (922) to drive the auger (106). The GPS sensor (902)

is housed in the equipment housing (206) to identify the location of the extracted soil sample. In an embodiment, the equipment housing (206) provides for ergonomic requirements for the handling of the device in use. To include, but not limited to, handholds for manipulation of the device during sampling and transport. In an embodiment, the equipment housing (206) provides a location for the systems controller (computer) integrated into the housing itself. In an embodiment, the equipment housing (206) provides a location for the systems controller (computer system) detachable from the auger and homogenization cylinder (206).

Figure 8:
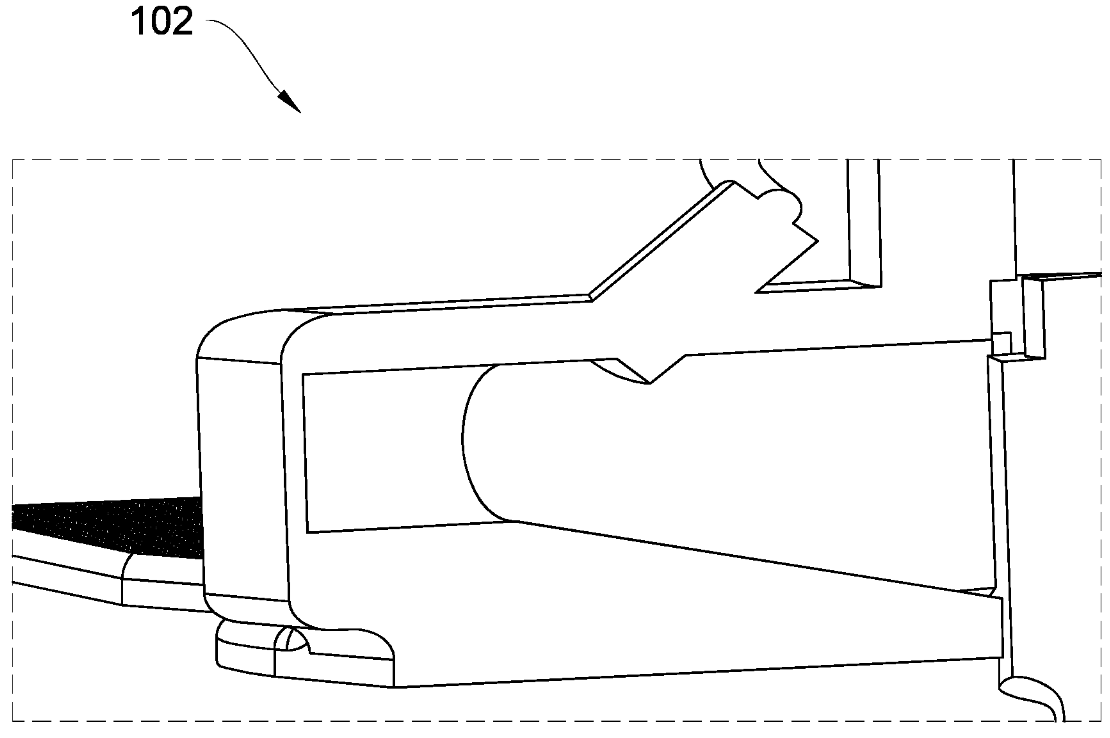
FIG. 8 illustrates a perspective view of a sampling chamber and soil expelling mechanism, in accordance with at least one embodiment.
Figure 9:
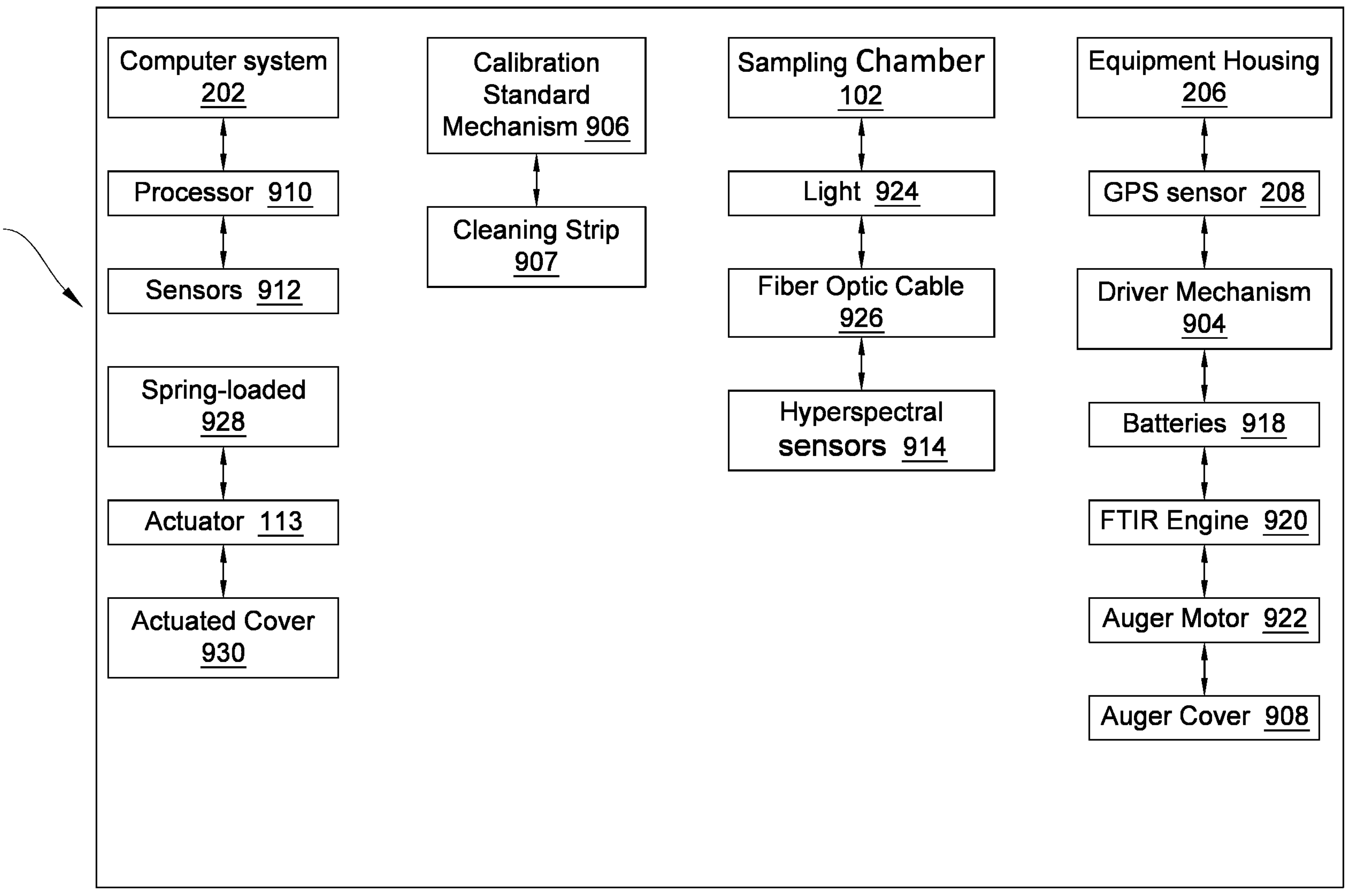
FIG. 9 illustrates various components of the present soil sampling device that are not depicted in FIGS. 1-8, in accordance with at least one embodiment.

FIG. 8 illustrates a perspective view of a sampling chamber (102) and soil expelling mechanism, in accordance with at least one embodiment. The sampling chamber (102) is configured to store the soil sample during one or more scans, which blocks ambient light to ensure accurate spectroscopy readings and provides a mechanism to support the disposal of the soil sample after testing. In an embodiment, the sampling chamber (102) comprises a light (924) and a fiber optic cable (926). In an embodiment, the sampling chamber (102) houses the sample and is of appropriate dimensions to ensure the probe consisting of a light source and fiber optic (112) is in adequate contact with the sample and the sample maintains adequate depth during testing to comply with the standard. The sampling chamber (102) creates an environment free of ambient light. The sampling chamber (102) provides adequate spacing to accommodate both the sample, the probe consisting of a light source and fiber optic cable (112), and the calibration standard. The sampling chamber (102) includes a feature for the elimination of the sample material between each sampling. Embodiment might include a trap door mechanism to expel the sample material. The sampling chamber (102) and the homogenization cylinder (136) include a feature to allow for the cleaning and removal of excess sample material. In one embodiment, the device includes two trap doors: 1) the Homogenization Cylinder Trap Door; and 2) the Sample Chamber Trap Door. The Homogenization Cylinder Trap Door provides access to the quick disconnect motor drive, facilitating the removal of the auger. Additionally, it can be utilized to access the inner diameter of the housing for cleaning purposes. The sample chamber trap door accommodates the sample and the probe consisting of a light source and fiber optic cable. After sampling, opening the sample trap door allows for easy removal and disposal of the sample material. This trap door also provides access to the face of the probe consisting of a light source and fiber optic cable for cleaning and calibration by inserting a calibration standard.

Figure 5:
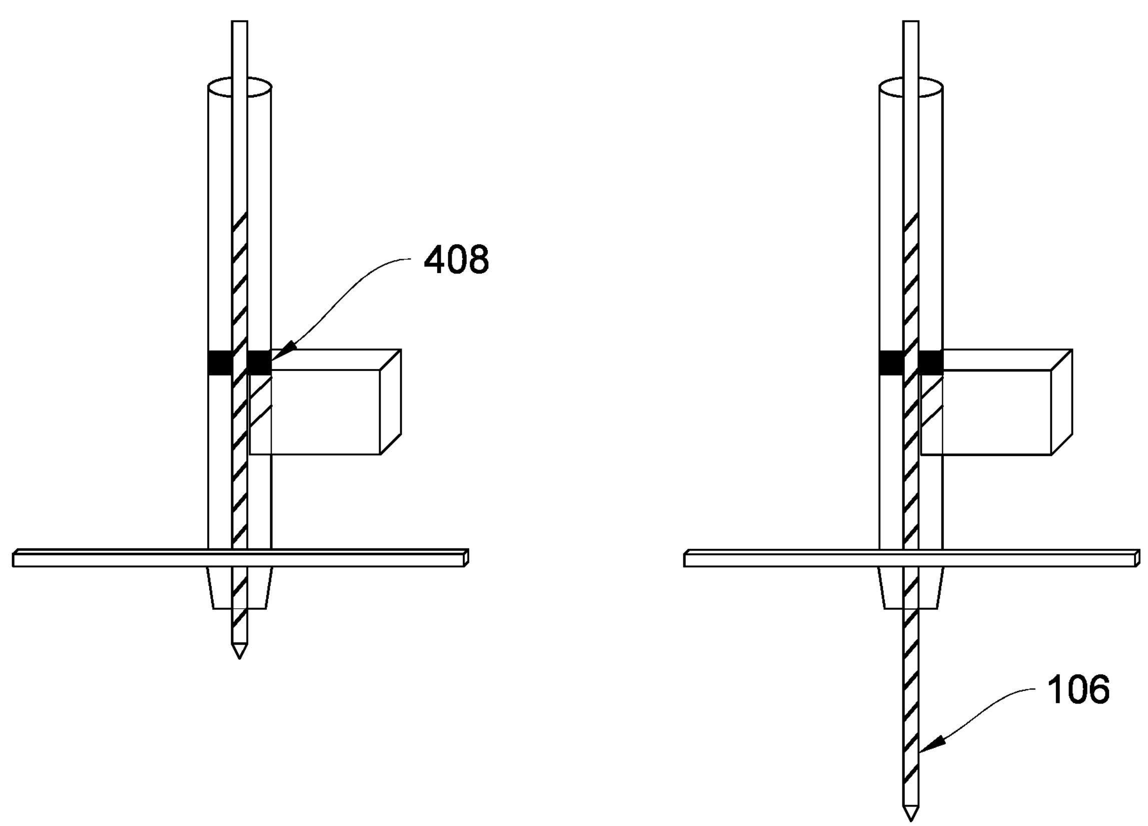
FIG. 5 illustrates a perspective view of an auger of the soil sampling device, in accordance with one embodiment of the present invention.

FIG. 5 illustrates a perspective view of an auger (106) and column interface bushings (408), in accordance with one embodiment of the present invention. FIG. 6 illustrates a closer view of the auger (106), in accordance with one embodiment of the present invention. The core rod column (104) and the auger (106) are configured to extract the soil sample. The auger (106) is configured to cut the soil, migrate the soil upward to the sampling chamber (102), and homogenize the material in the first stage. In an embodiment, the auger (106) or the sampling element/auger cover (908) retracts and advances to a specified depth during use to allow for sample capture and containment. In an embodiment, the auger (106) is attached to a motor drive via the quick disconnect (110). As shown in FIG. 1, the movement of the auger (106) is about six inches. The driver mechanism (904) is housed in the equipment housing to drive the auger and core rod column to extract the soil sample. In operation, the sampling element/auger cover (908) remains stationary against or just below the sample surface. As the sampling element/auger (106) digs into the soil, it exits the cover, and the walls of the resulting hole along with the cover act as a containment mechanism for the sample, forcing the material up the auger through the hole and the cover and into the sample chamber. The auger is also designed to retract into the cover to protect the user from the rotating blade. When the auger is not in use, the spring-loaded cover remains stationary, and level with the ground. As the auger moves into the soil, it extends beyond the cover. Upon retraction, the auger pulls back into the cover to minimize operator exposure to moving parts. The length of the spring-loaded portion of the cover controls the depth of auger travel, which can be adjusted using a stop pin. The auger return can be facilitated by either springs or hydraulic actuators.

The homogenization cylinder (136) is configured to support the equipment housing (206) and the sampling chamber (102). The homogenization cylinder (136) encloses the auger (106) and the driver mechanism and provides an area for mixing and homogenization of the soil sample. In an embodiment, the homogenization cylinder (136) comprises an opening to allow for cleaning and removal of debris. Both the sampling chamber (102) and the homogenization cylinder (136) feature a trap door. Additionally, there is a port designed to facilitate the cleaning of the quick disconnect. In one embodiment, an auger rod is connected to the auger driver via a quick disconnect located at the top of the sampling element/auger cover. If the auger becomes obstructed with sample material, the operator can pull up on the quick disconnect at the motor driver to release it from the system, allowing it to slide out of the cover housing for cleaning. Once cleaned, it can be pushed back into the housing, where it will reconnect to the driver with pressure using the quick disconnect. The advantage of having a removable auger assembly is ease of use for the operator. Cleaning the auger separately from the system facilitates easier cleaning and reduces the risk of damaging the electrical components of the sampling device. In one embodiment, a clean auger results in a more accurate representation of the sample.

The stomp pad (108) is configured to control the depth of the soil sampling and to provide support during the actuation of the auger (106). In an embodiment, the stomp pad (108) is configured to control the depth of the auger (106) and to facilitate the operational stability of the soil sampling device (100).

In an embodiment, the spectral sensors (912) are capable of NIR Spectrometry in the range of 350 to 2500 nm. The calibration standard mechanism (906) is configured to move a calibration standard in and out of a sensor view for calibration. The calibration standard mechanism (906) includes a cleaning strip to wipe the standard and/or probe before calibration to ensure accuracy. According to an embodiment herein, the calibration standard mechanism (906) is a sliding plate that moves into and out of the scan path to allow the system to read it for calibration. Essentially, it is a white plate that serves as a baseline for the sensor. In an embodiment, the calibration standard mechanism (906) can be moved in front of the probe to allow for calibration and then retracted to allow for scanning. In an embodiment, the calibration standard mechanism (906) has an automatic cleaning feature to ensure correct calibration. An embodiment of the calibration standard mechanism (906) includes a wiping structure to wipe the calibration standard as it is moved to and from its position in front of the probe consisting of a light source and fiber optic cable.

The sampling element/auger cover (908) is configured to retract and advance during the soil sample collection to ensure sample capture and containment. The quick disconnect (110) is configured to allow for the removal of the auger (106) for cleaning and removing debris. In an embodiment, the soil sampling device (100) includes either a spring-loaded (928) or an actuated cover (930) for the auger (106). In an embodiment, the spring-loaded (928) or the actuated cover (930) comprises sampling column bushings (402) to control a sampling depth.

The probe consisting of a light source and fiber optic cable is a soil probe (112) that is configured to scan the soil sample. In an embodiment, the sampling element (106) is a motor-driven auger-type device, capable of pulling a specified volume sample over a fixed depth (1-30 inches). In an alternative embodiment, sampling element is a manual tube, capable of pulling the specified volume sample over the fixed depth (1-30 inches). In one embodiment, the sampling element (106) must have a sufficient length to accommodate a travel distance of 1-30 inches. Additionally, the motor torque must be adequate to maintain the auger speed as the device penetrates deeper into the sample core site. In another embodiment, the auger should be easily accessible for cleaning to ensure that samples accurately represent individual sites. Furthermore, a reversible auger driver motor may be utilized to facilitate cleaning and debris removal. The diameter and length of the auger must be appropriately sized to extract an adequate sample volume. The auger material must possess sufficient strength to support the sample, withstand the forces required for extraction, and endure the torque applied by the auger driver. The sampling element/auger cover should support the auger position without hindering its movement (rotation). The depth of the auger must be adjustable to accommodate multiple sampling depths, and the angle of the auger blades should facilitate vertical travel of the sample to the sampling chamber. In an exemplary embodiment, the sampled volume will vary based on the depth of the sample (not a fixed volume for all depths, but a consistent volume at each depth). The sample volume is designed to meet ASTM requirements for pulling a 6-inch core. The sample chamber must be sized to accommodate varying sampling volumes. Both the auger and the sampling element/auger cover must be robust enough to withstand sample and testing conditions, including water, mud, temperature variations, etc., utilizing materials such as Teflon, stainless steel, anodized aluminum, etc.

In an embodiment, the auger (106) homogenizes the soil sample during transport through the homogenization cylinder (136) to the sampling chamber (102). In an embodiment, the auger (106) and the homogenization cylinder (136) capture the soil sample in its entirety and transport it to the sampling chamber (102). According to an embodiment herein, two cylinders move relative to one another: the homogenization cylinder (208) and the core rod column (104). The lower cylinder is the homogenization cylinder (136), and the upper one is the core rod column (104).

In an embodiment, the auger (106) works as a vehicle to homogenize the sample during transport through the homogenization cylinder/tube/barrel to the sampling chamber. This is accomplished through the mixing action within the auger and during the expulsion of the sample from the auger (106) into the sampling chamber (102).

Figure 10:
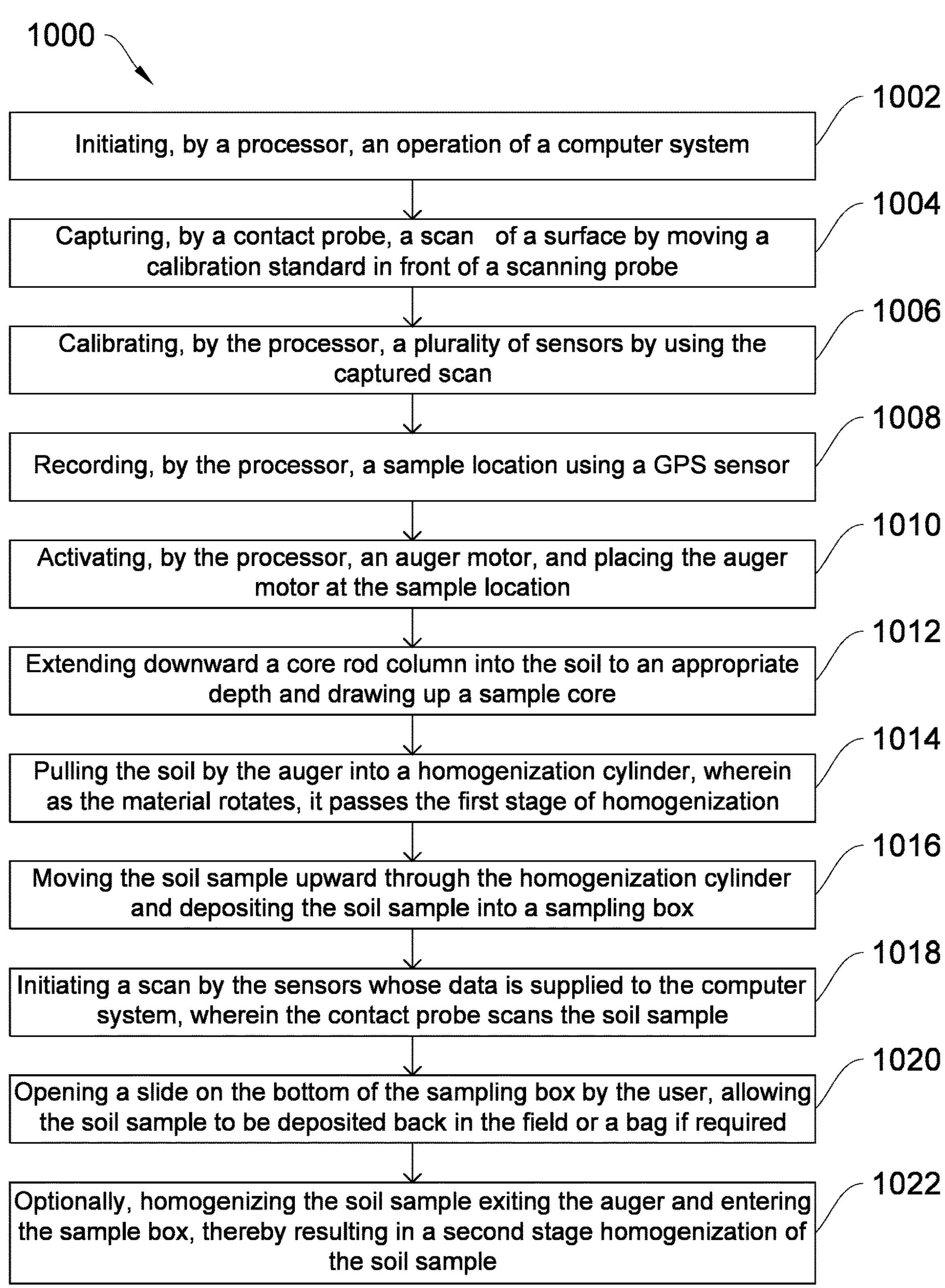
FIG. 10 illustrates a flowchart of a method to create one or more soil maps by collecting one or more soil samples, in accordance with at least one embodiment.

FIG. 10 illustrates a flowchart of a method 1000 to create one or more soil maps by collecting one or more soil samples, in accordance with at least one embodiment. The method 1000 includes a step 1002 of initiating, by a processor, an operation of a computer system. The method 1000 includes a step 1004 of capturing, by a probe consisting of a light source and fiber optic cable, a scan of a surface by moving a calibration standard in front of a probe. In an embodiment, the probe consisting of a light source and fiber optic cable and spectral sensors capture the calibration standard's spectral footprint. This sets the baseline and the other scans measure from there. The method 1000 includes a step 1006 of calibrating, by the processor, a plurality of spectral sensors by using the captured scan. The method 1000 includes a step 1008 of recording, by the processor, a sample location using a GPS sensor. The method 1000 includes a step 1010 of activating, by the processor, an auger motor and placing the auger motor at the sample location. The method 1000 includes a step 1012 of extending downward a core rod column into the soil to an appropriate depth and drawing up a sample core. The method 1000 includes a step 1014 of pulling the soil by the auger into a homogenization cylinder, wherein as the material rotates, it passes the first stage of homogenization. The method 1000 includes a step 1016 of moving the soil sample upward through the homogenization cylinder and depositing the soil sample into a sampling chamber. The method 1000 includes a step 1018 of initiating a scan by the spectral sensors whose data is supplied to the computer system. According to an embodiment herein, the probe consisting of a light source and fiber optic cable transmits the light signature through a fiber optic cable. The hyperspectral sensors convert that to a measure of reflected wavelength and intensity, and the software then converts that into a nutrient map based on an algorithm. In an embodiment, the probe consisting of a light source and fiber optic cable in the soil sampling device scans the soil sample. In an embodiment, the sampling element is a motor-driven auger-type device, capable of extracting a specified volume sample at a fixed depth ranging from 1 to 30 inches. In an embodiment, the sampling element is a manual tube, capable of extracting the specified volume sample at a fixed depth ranging from 1 to 30 inches.

The method 1000 includes a step 1020 of opening a slide on the bottom of the sampling chamber by the user, allowing the soil sample to be deposited back in the field or a bag if required. The method 1000 optionally includes a step 1024 of homogenizing the soil sample exiting the auger and entering the sample chamber, thereby resulting in a second stage of homogenization of the soil sample. In an embodiment, the auger or sampling element/auger cover is configured to retract and advance to a specified depth during operation to facilitate sample collection and containment. In an embodiment, the stomp pad is configured to regulate the depth of the auger and enhance the operational stability of the soil sampling device.

Unless otherwise defined, all terms (including technical and scientific terms) used in this disclosure have the same meaning as commonly understood by one of ordinary skill in the art to which this disclosure belongs. It is to be understood that the phrases or terms employed of the present invention are for description and not of limitation. As will be appreciated by one of the skills in the art, the present disclosure may be embodied as a device, system, and method, or computer program product. Further, the present invention may take the form of a computer program product on a computer-readable storage medium having computer-usable program code embodied in the medium. The present systems and methods have been described above with reference to specific examples. However, other embodiments and examples than the above description are equally possible within the scope of the present invention. The scope of the disclosure may only be limited by the appended patent claims. Even though modifications and changes may be suggested by the persons skilled in the art, it is the intention of the inventors and applicants to embody within the patent warranted heron all the changes and modifications as reasonably and properly come within the scope of the contribution the inventors and applicants to the art. The scope of the embodiments of the present invention is ascertained with the claims to be submitted at the time of filing the complete specification.

What is claimed is:

1. A soil sampling device, comprising:

a computer system configured to store and process data related to a location of a soil sampling and spectral data and to display the collected scan data on a display screen;

an equipment housing configured to support the computer system;

a GPS sensor housed in the equipment housing to identify a location to extract the soil sample;

a sampling chamber configured to store the soil sample during one or more scans, which blocks ambient light to ensure accurate spectroscopy readings and provides a mechanism to support the disposal of the soil sample after testing;

a core rod column and a sampling element configured to extract the soil sample, wherein the sampling element is configured to cut the soil, migrate the soil upward to the sampling chamber, and homogenize the material in a first stage;

a driver mechanism housed in the equipment housing to drive the sampling element and core rod column to extract the soil sample;

a homogenization cylinder configured to support the equipment housing and the sampling chamber, wherein the homogenization cylinder encloses the sampling element and the driver mechanism and provides an area for mixing and homogenization of the soil sample;

a stomp pad configured to control the depth of the soil sampling and to provide support during the actuation of the sampling element;

an sampling element cover configured to retract and advance during the soil sample collection to ensure sample capture and containment;

a quick disconnect configured to allow for the removal of the sampling element for cleaning and removing debris; and a probe consisting of a light source and fiber optic cable configured to scan the soil sample.

2. The soil sampling device as claimed in claim 1, comprises a calibration standard mechanism configured to move a calibration standard in and out of a sensor view for calibration, wherein the calibration standard mechanism comprises a cleaning strip to wipe the standard or the sensor before calibration to ensure accuracy.

3. The soil sampling device as claimed in claim 1, wherein the computer system comprises a processor configured to calibrate a plurality of spectral sensors using a plurality of software algorithms.

4. The soil sampling device as claimed in claim 1, wherein the equipment housing houses a plurality of components comprising: one or more hyperspectral sensors (IR, NIR, SWIR), a plurality of batteries, an FTIR engine, and an auger motor to drive the auger.

5. The soil sampling device as claimed in claim 1, wherein the sampling chamber comprises a light and a fiber optic cable.

6. The soil sampling device as claimed in claim 1, wherein the auger or a sampling element is a motor-driven auger type device, capable of pulling a specified volume sample over a fixed depth.

7. The soil sampling device as claimed in claim 6, wherein the sampling element is a manual tube, capable of pulling the specified volume sample over the fixed depth.

8. The soil sampling device as claimed in claim 1, wherein the auger or the sampling element/auger cover retracts and advances to a specified depth during use to allow for sample capture and containment.

9. The soil sampling device as claimed in claim 1 comprises one or more of a spring-loaded and an actuated cover for the sampling element/auger, wherein the spring-loaded comprises a stop to control a sampling depth.

10. The soil sampling device as claimed in claim 1, wherein the stomp pad is configured to control the depth of the sampling element/auger and to facilitate operational stability of the soil sampling device.

11. The soil sampling device as claimed in claim 1, wherein the sampling element/auger is attached to a motor drive via the quick disconnect.

12. The soil sampling device as claimed in claim 1, wherein the homogenization cylinder comprises an opening to allow for cleaning and removal of debris.

13. The soil sampling device as claimed in claim 1, wherein the sampling element/auger homogenizes the soil sample during transport through the homogenization cylinder to the sampling chamber.

14. The soil sampling device as claimed in claim 1, wherein the sampling element/auger and the homogenization cylinder capture the soil sample in its entirety and transport it to the sampling chamber.

15. A method to create one or more soil maps by collecting one or more soil samples, comprising:

initiating, by a processor, an operation of a computer system;

capturing, by a probe consisting of a light source and fiber optic cable, a scan of a surface by moving a calibration standard in front of the probe;

calibrating, by the processor, a plurality of spectral sensors by using the captured scan;

recording, by the processor, a sample location using a GPS sensor;

activating, by the processor, an auger motor, and placing the auger motor at the sample location;

extending downward a core rod column into the soil to an appropriate depth and drawing up a sample core;

pulling the soil by the sampling element/auger into a homogenization cylinder, wherein as the material rotates, it passes the first stage of homogenization;

moving the soil sample upward through the homogenization cylinder and depositing the soil sample into a sampling chamber;

initiating a scan by the spectral sensors whose data is supplied to the computer system, wherein the probe consisting of a light source and fiber optic cable scans the soil sample; and opening a slide on the bottom of the sampling chamber by the user, allowing the soil sample to be deposited back in the field or a bag if required.

16. The method as claimed in claim 15, optionally, comprises a step of homogenizing the soil sample exiting the homogenization cylinder/auger cylinder and entering the sample chamber, thereby resulting in a second stage homogenization of the soil sample.

17. The method as claimed in claim 15, wherein the sampling element is a motor-driven auger-type device, capable of extracting a specified volume sample at a fixed depth ranging from 1 to 30 inches.

18. The method as claimed in claim 15, wherein the sampling element is a manual tube, capable of extracting the specified volume sample at a fixed depth ranging from 1 to 30 inches.

19. The method as claimed in claim 15, wherein the auger or sampling element/auger cover is configured to retract and advance to a specified depth during operation to facilitate sample collection and containment.

20. The method as claimed in claim 15, wherein the stomp pad is configured to regulate the depth of the sampling element/auger and enhance the operational stability of the soil sampling device.

* * * * *